United States Patent [19]
Annis

[11] Patent Number: 5,224,144
[45] Date of Patent: Jun. 29, 1993

[54] REDUCED MASS FLYING SPOT SCANNER HAVING ARCUATE SCANNING LINES

[75] Inventor: Martin Annis, Cambridge, Mass.

[73] Assignee: American Science and Engineering, Inc., Cambridge, Mass.

[21] Appl. No.: 758,101

[22] Filed: Sep. 12, 1991

[51] Int. Cl.$^5$ .............................................. G21K 5/10
[52] U.S. Cl. ...................... 378/146; 378/57; 378/86; 378/87; 378/147; 378/156
[58] Field of Search ................... 378/4, 57, 86, 87, 62, 378/44, 146, 901, 89, 19, 147, 156

[56] References Cited

U.S. PATENT DOCUMENTS 4,179,100 12/1979 Sashin et al. ..................... 378/19
5,022,062 6/1991 Annis ................................ 378/87

Primary Examiner—David P. Porta
Assistant Examiner—Kim-Kwok Chu
Attorney, Agent, or Firm—Pollock, Vande Sande & Priddy

[57] ABSTRACT

A method and apparatus for creating image information for objects inspect with penetrating radiation which utilizes a flying spot scanner of reduced mass. Objects are scanned with penetrating radiation along curved scan lines. The flying spot scanner which effects such scanning has a stationary absorber plate having a fixed slit in it which is curved, as well as a chopper wheel having radially oriented slits. As the chopper wheel rotates, the radially oriented slits traverse the projection of the radiation passing through the fixed slit, and because this slit is curved, the radial slits may be of reduced length, and the chopper wheel may be of reduced mass. The detected radiant energy is divided into pixels, and the pixels are addressed to a utilization means such as a memory or a display in such manner that the pixels which correspond to a scan line of the object define a curved line in the utilization means which has the same shape as the curved scanning line.

16 Claims, 3 Drawing Sheets

PRIOR ART

REDUCED MASS FLYING SPOT SCANNER HAVING ARCUATE SCANNING LINES

BACKGROUND OF THE INVENTION

The present invention is directed to an improved method and apparatus for imaging objects with penetrating radiation.

The use of penetrating radiant energy is well known in the imaging of both inanimate and animate objects. As an example, systems of this type find important use in the inspection of objects to discover secreted contraband which may present a security threat.

One type of inspection system uses a flying spot of penetrating radiation to scan the object being inspected. After interaction with the object, the radiant energy may be incident on detector(s) which detect transmitted and/or scattered energy. For example, such a system is disclosed in U.S. Pat. No. Re 28,544, assigned to American Science and Engineering, Inc. This type of system is an improvement over the prior art, in that it allows operation without exposing personnel to excessive radiation. An additional advantage is that since the object may be divided into elemental frontal areas which ar scanned by the flying spot, and the detector signal may be time divided into intervals denoted as pixels which correspond to these elemental areas, the radiant energy which is incident on either a transmission or scatter detector at any given time may be referred to a particular elemental area of the object.

In such a flying spot inspection system, the apparatus for producing the flying spot includes a source of penetrating radiation, an absorber plate of highly absorbing material, preferably a high Z material such as lead which has a fixed slit therein, and a chopper wheel, which also must be made of highly absorbing material. The chopper wheel has radially directed slits, and when the chopper wheel is rotated, these slits rotate past the fixed slit in the absorber plate. As such rotation occurs, a flying spot of radiation is created along the direction of the fixed slit in the absorber plate, which is used to scan the object being inspected. Additionally, the system is arranged so that there is relative translation movement between the object and flying spot in a direction perpendicular to the scanning direction of the flying spot, so that the entire object is scanned in successive lines.

In the prior art flying spot scanning system, the flying spot is scanned in straight lines, which typically lie in the vertical or horizontal direction. This follows from the fact that the fixed slit in the absorber plate, which defines the scanning direction, is inevitably a straight line in the prior art. With such a system, in order to provide a scan line of adequate length, the radial slits in the chopper wheel, which must maintain coincidence with the projection of the radiation passing through the fixed slit as the wheel rotates, must be of substantial length.

While the flying spot scanning system described above has many advantages over the prior art, a problem with it is that because the radial slits must be of substantial length, it is necessary for the chopper wheel to have so much mass, that at the rotation speeds which are required for some applications, it may break apart. Additionally, the high mass of the wheel requires that a powerful motor be used, which may increase the expense of the equipment. By way of example, in a chopper wheel of current design, an annular disk or doughnut of lead which contains the radial slots is embedded in an aluminum wheel. For a typical application, the length of the radial slots must be 14.6 cm, which also defines the radius of the doughnut. Since the thickness of lead required is about 2.15 cm, the resultant weight of the lead doughnut is about 510 lbs (230 Kg.).

SUMMARY OF THE INVENTION

It is therefore an object of the present invention to provide a method and apparatus of imaging radiation which uses a chopper wheel having reduced mass.

It is a further object of the invention to provide a flying spot scanner which uses a chopper wheel which may be rotated at higher speeds.

It is still a further object of the invention to provide a flying spot scanner which uses a chopper wheel which may be more easily rotated.

In accordance with the invention, the above objects are accomplished by scanning an object with a flying spot of penetrating radiation along curved scan lines. The use of such curved scan lines permits a flying spot scanner of more advantageous structure to be used.

After the radiant energy interacts with the object being inspected, it is detected, and a detection signal is provided which is divided into pixels, wherein each pixel corresponds to an elemental frontal area of the object being inspected. The pixels are addressed to a utilization means such as a memory or a display in such manner that the pixels which correspond to a scan line of the object define a curved line in the utilization means which has the same shape as the curved scanning line. In this way, a proper image of the object is presented.

In the preferred embodiment of the invention, the object is scanned with a flying spot of penetrating radiation along arcuate scan lines, wherein the term "arcuate" refers herein to curved scanning lines having the shape of a circular arc The pixels representative of the scanning are addressed to a utilization means such that the pixels which correspond to a scan line define an arcuate line in the utilization means.

In a flying spot scanner in accordance with a preferred embodiment of the invention, a source of penetrating radiation, an absorber plate having a fixed, arcuate slit, and a chopper wheel are provided. The chopper, wheel has an insert of high Z material in the shape of an annular ring or doughnut, which has relatively short radial slits therein. As the chopper wheel is rotated, the radially directed slits maintain coincidence with the projection of the penetrating radiation which passes through the fixed slit in the absorber plate, to form a flying spot along an arcuate path. Additionally, means for providing relative translation motion between the fixed slit and the object being illuminated is provided, so that the object is scanned in successive, arcuate scanning lines.

BRIEF DESCRIPTION OF THE DRAWINGS

The invention will be better understood by referring to the accompanying drawings, wherein.

DETAILED DESCRIPTION OF THE PREFERRED EMBODIMENT

Figure 1:
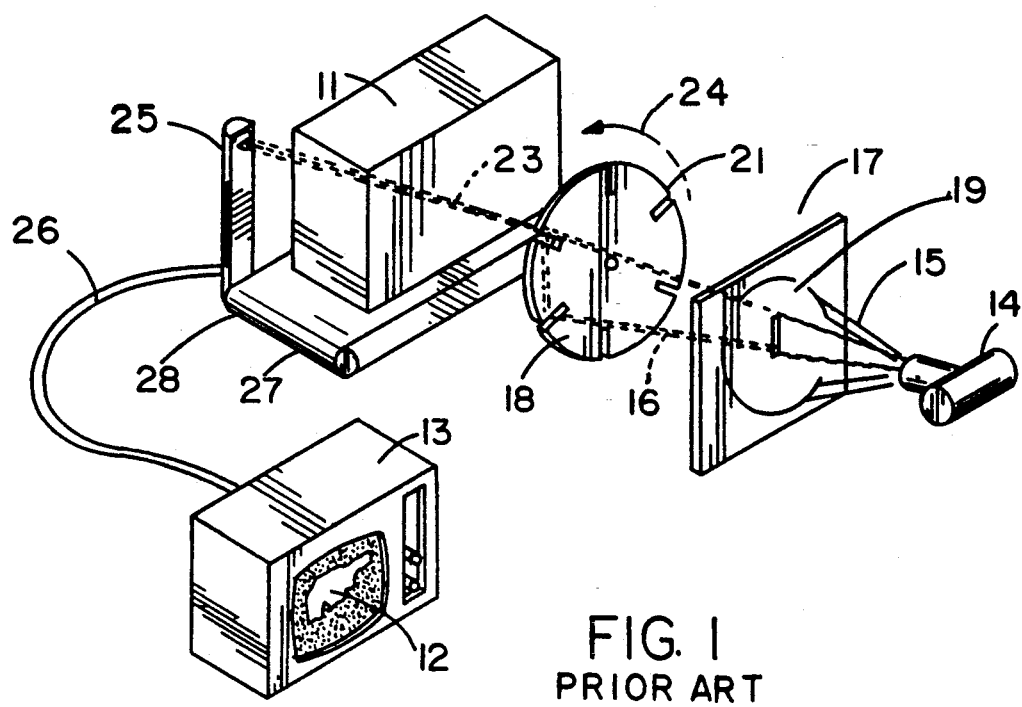
FIG. 1 shows the prior art flying spot scanner system.

Referring to FIG. 1, an imaging system which uses a flying spot scanner in accordance with the teachings of the prior art is illustrated. The system uses penetrating radiation such as x-rays to inspect object for contraband, and is operative to display relevant information on monitor 13.

Referring to the figure in greater detail, an x-ray source 14 is seen to provide a generally conical beam of x-rays 15, which are collimated into a fan beam 16 by fixed slit 19 in absorber plate 17. The fan beam is incident upon the rotating chopper wheel 18 formed with an array of peripheral radial slits, such as 21, for intercepting the fan beam to produce a pencil beam. The pencil beam 23 scans object 11 and radiation sensitive detector 25 from top to bottom as chopper wheel 18 rotates in the direction of arrow 24. The scanning pencil beam 23 is also known as a flying spot. The detector 25 provides an image signal output on line 26, which is transmitted to video storage and display unit 13 to produce the desired image 12 as conveyor 27 carries object 11 in the direction of arrow 28 across the vertical scanning lines.

The geometry and timing of the system is arranged so that each slit 21 causes a new pencil beam or flying spot to strike the top of detector 25 just after the previous pencil beam has swept past the bottom of the detector. That is to say, the height of fan beam 16 corresponds substantially to the separation between adjacent ones of slits 21 at substantially the maximum radial distance from the edge of disc 18 where the slits intercept fan beam 16. While FIG. 1 shows the elements that provide the flying spot source in exploded form to better illustrate the principles of the invention, the elements 14, 17 and 18 are preferably housed relatively close together in an enclosure that shields radiation, so that the only significant radiant energy that escapes is in pencil beam 23.

As object 11 moves past the line being scanned, it differentially attenuates the x-rays in pencil beam 23 incident upon detector 25 so that the electrical signal provided on output line 26 is amplitude modulated in proportion to the instantaneous x-ray flux incident upon it. This signal thus corresponds to a vertical line image of the transmissivity of parcel 11 and is analogous to one scan line of a television video signal. As parcel moves horizontally past the line being scanned, sequential pencil beams intercept slightly displaced regions of parcel 11 so that the corresponding electrical signals from detector 25 may be appropriately displayed line-by-line to produce a two dimensional image of object 11 in x-rays analogous to the display of a picture on a television monitor as formed by line-by-line images. The output of detector 25 may thus be processed in accordance with the same storage and display techniques used in conventional video systems to store and display single raster images.

Figure 2:
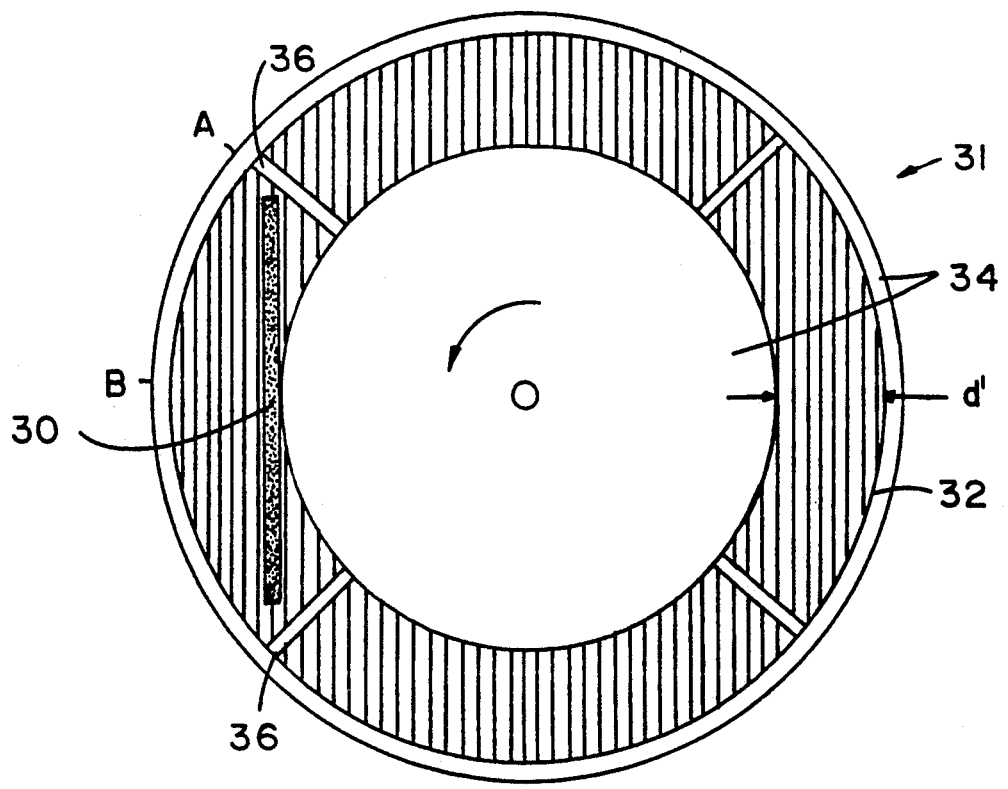
FIG. 2 is a detailed view of the scanner of FIG. 1, which shows how the flying spot is formed.

Referring to FIG. 2, it is seen in greater detail how the pencil beam 23 is formed. In this figure, slit 30 is a projection of the fixed slit of the stationary absorber plate, which is made of a high Z material such as lead. Further, in the embodiment shown in FIG. 2, chopper wheel 31 is comprised of an annular disk or doughnut shaped insert 32 of a high Z material such as lead, which is inserted in- aluminum wheel 34. The-lead doughnut has a plurality of radially oriented slits 36 disposed therein.

As the wheel rotates, a radially oriented slit 36 passes over the projection of the radiation passing through fixed slit 30, thus forming the pencil beam. It follows from this that the length of the radial slits is dependent on the required scan length of the pencil beam. Thus, it is seen that as the wheel rotates from point A to point B in FIG. 2, half the length of the fixed slit 30 is covered, and near point A, the pencil beam is formed by the fixed slit and the outside area of the radial slit, while near point B it is the fixed slit and the inside area of the radial slit which forms the beam.

The fact that the radial slits must be of a certain minimum length to accomplish proper scanning has led to a problem in the system of the prior art. This is because, as may be seen by referring to FIG. 2, the length of the radial slits dictates the width d of the lead annular or doughnut, which in turn, at least in part, controls how heavy the lead annular is. It has been found that with the system of the prior art, the lead annular is so heavy, that at the rotation speeds which are necessary for certain applications, it beaks apart. Additionally, a powerful motor is required to rotate the heavy chopper wheel at such speeds.

Referring to an illustrative example, in a planned design, a 380 KV x-ray source is used, and to sufficiently absorb the x-rays from such a source, the required thickness of the lead doughnut is about 2 inches (approx. 5 cm), while the required radius R of the wheel to the outer edge of the lead is about 20 inches (approx. 50 cm).

The width of the lead doughnut d, in FIG. 2, is given by:

$$d = R(1 - \cos \pi/n)$$

where n = the number of radial slits.

In this design, n=4, so that $d = 50(1 - \cos 45°) = 14.6$ cm.

In this case, the width of a typical radial slit (and fixed slit) opening is 4 mm. The weight of the lead doughnut which is necessary to achieve these dimensions is about 510 lbs (approx. 230 Kg.).

Figure 3:
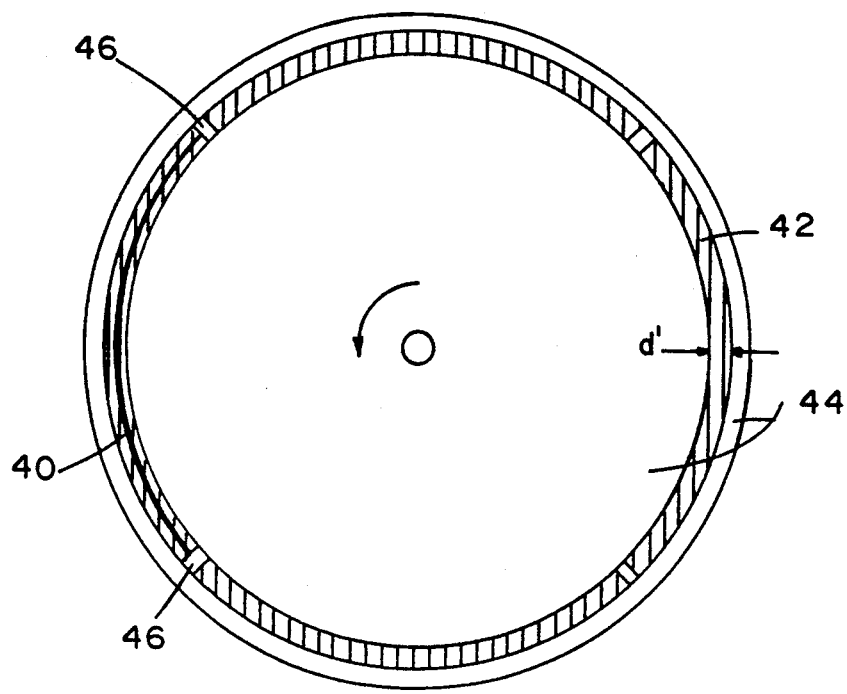
FIG. 3 is a detailed view of an embodiment of the scanner of the present invention.

Referring to FIG. 3, a detailed view of a portion of a flying spot scanner in accordance with an embodiment of the present invention is shown. In accordance with this embodiment, is seen that fixed slit 40 in the stationary absorber plate is arcuate rather than straight. A ring 42 of high Z material is provided in a wheel of aluminum or other material 44, as in the prior art, but it is noted that the length of radial slits 46 may be made much shorter than in the case of the prior art. This is because the fixed slit and the doughnut of high Z material are functionally coincide with each other, and as the wheel rotates, the length of the radial slit continuously overlies the projected radiation which passes through the fixed slit.

The result of the modification shown in FIG. 3 is that the required slit length is only 2 cm as opposed to 14.6 cm. With a slit width of 4 mm in both the rotating wheel and the fixed absorber plate, the weight of the lead ring is only about 36 Kg (80 lbs.), or about less than 1/6 of the weight of the lead doughnut which was in the prior art embodiment. The lower weight provided by the present invention is much more manageable, and permits rotation of the scanning wheel at high speeds without structural problems developing. Additionally, it permits a less powerful motor to be used to effect rotation.

It should be noted that in the preferred embodiment of FIG. 3, the radius of the fixed slit 40 is such that as the chopper wheel rotates, the high Z insert 42 and slits 46 follow exactly the curve of the radiation passing through the fixed slit. In this regard, it is noted in FIG. 3, that high Z insert 42 and the projection of fixed slit 40 are drawn as being coincident with each other. However, it should be appreciated that the projection of slit 40 may be in the shape of a curve of larger radius than is illustrated. In this case, the slits 46 would not exactly follow the curve of the fixed slit as they rotate; however, in this case, the radial slits may still be made smaller than when the fixed slit is a straight line, although not so small as is illustrated in FIG. 3.

Figure 4:
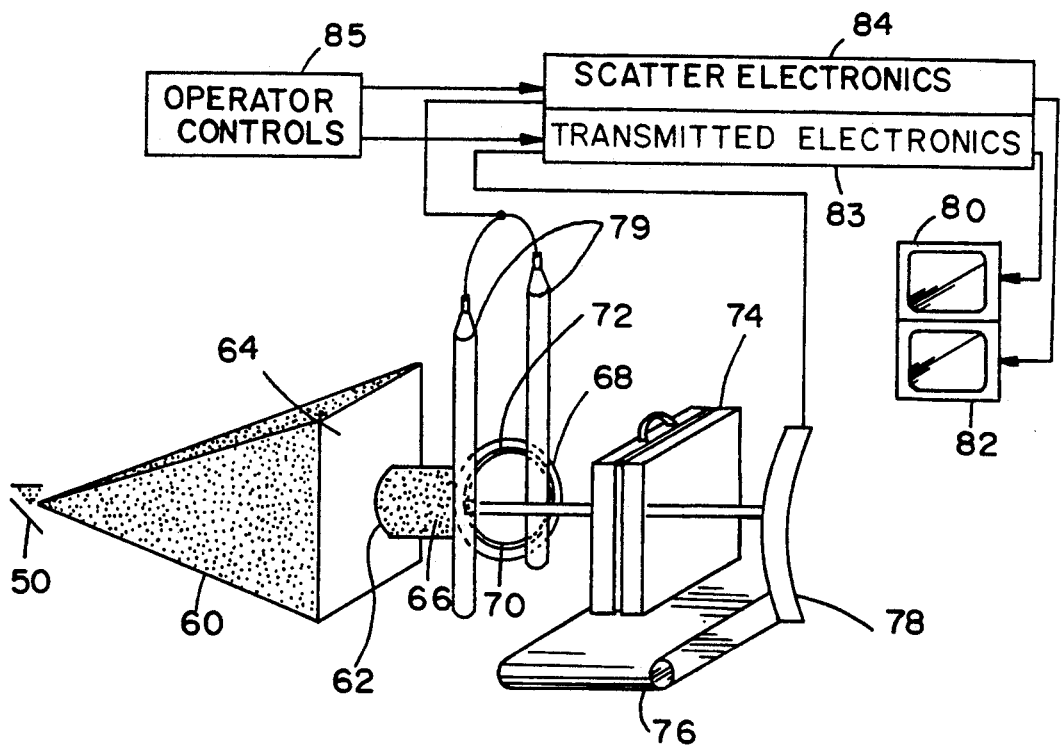
FIG. 4 illustrates an embodiment of the present invention.

Referring to FIG. 4, an inspection system which incorporates the present invention is shown. In this figure, x-ray source 50 produces conical beam 60, which is fed through arcuate slit 62 in absorber plate 64 to produce an arcuately shaped fan beam 66, which is incident on chopper wheel 68. Chopper wheel 68 has lead ring 70 therein, which contains radial slits 72. As the wheel 68, is rotated, flying spot scanning in arcuate lines is accomplished.

Object 74 is transported on conveyor 76 past the scanning beam. Transmission detector 78 is provided, which it is noted is also arcuately shaped, so that the scanning pencil beam which is transmitted through the object 74 is incident on the detector over the length of the scan line. Additionally, backscatter detectors 79 may also provided, and if the particular system calls for them, forward scatter detectors may be provided as well.

The outputs of detectors 78 and 79 are digitized, and are divided into pixels, each of which corresponds to an elementary unit of frontal area of the object which is scanned. The pixels are stored and/or displayed, and in the specific system of FIG. 4, which is shown only for the purposes of illustration, separate images of transmitted and scattered image information are provided in displays 80 and 82.

Since the scanning which is provided is in arcuate lines, there must be some provision made for addressing a utilization means such as a memory or a display in such manner that an accurate representation of the desired image is obtained. In accordance with the invention, this is accomplished by addressing the utilization means so that an arcuate scan line of the object being scanned is defined in the utilization device by an arcuate line of pixels.

Figure 5:
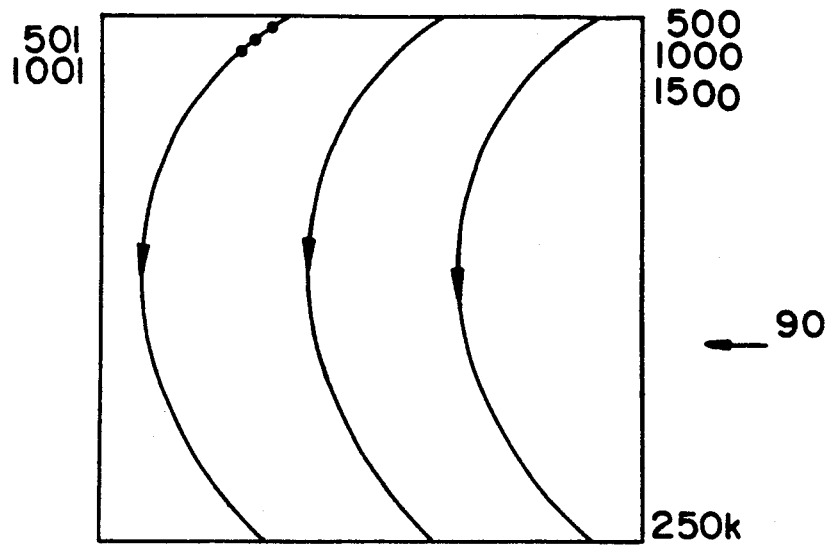
FIG. 5 illustrates the addressing of a utilization means.

Referring to FIG. 5, a utilization means such as a memory device 90 is depicted in schematic form. Each storage location in the memory is given a number, and for purposes of illustration the memory is considered to have 500 rows and 500 columns, resulting in 250 K storage locations. The pixels corresponding to certain, spaced apart scan lines of the object are illustrated in FIG. 5, and are seen to define respective arcuate lines of pixels in the memory. If this memory were to be read out in conventional raster fashion to a display, a proper image of the object information would result.

The addressing of the memory with image information is explained with reference to FIG. 6, which shows a block diagram of the components which may accomplish the addressing function. Referring to this figure, detection means 100 is a detector of radiant energy such as a transmission or scatter detector, or some combination thereof, which detects the radiation after it interacts with the object which is being inspected. The signal which is outputted by detection means 100 will in general have a varying magnitude, as determined by the atomic number, density, and thickness of the part of the object which is being instantaneously scanned. This magnitude is digitized in analog to digital converter 102.

As mentioned above, the detected signal is divided into pixels, each of which corresponds to an elementary frontal area of the object being scanned. This may be accomplished by clock 104, and scan counter 106, which are shown in FIG. 6. Clock 104 is arranged to count up to the number of pixels which are determined to be in a single scan line, and then reset itself. The number value of the signal appearing on clock output line 110 is thus indicative of the position of the instantaneous pixel being scanned within a scan line. Scan counter 106 is arranged to count to the number of pixels in a scan line, and then reset itself, while incrementing the number value of the signal on output line 114. Thus, the signals on lines 110 and 114 taken together are representative of the instantaneous pixel number which is being scanned at any time.

These signals are inputted to look up table 116. For each pixel number, look up table 116 has a corresponding memory address stored. These memory addresses are determined after consideration of the precise shape and dimensions of the arcuate scanning path which is effected by the scanner shown in FIGS. 3 and 4, as well as the number of pixels into which each scan line is divided.

For example, referring to FIG. 5, as an example, the first pixel which is scanned may be inputted to memory address No. 150, the second pixel may be inputted to address No. 610, the third may be inputted to address No. 1070, and so forth. As the object is scanned, each successive scan line is defined in the memory by an arcuate line of pixels which corresponds in shape to the original scanning line. Thus, referring again to FIG. 6, the magnitude value of each pixel occurs on line 118 at the output of analog to digital converter 102, and the address in the memory 90 to which it is routed is determined by the address signal on line 120, at the output of look up table 116.

Figure 6:
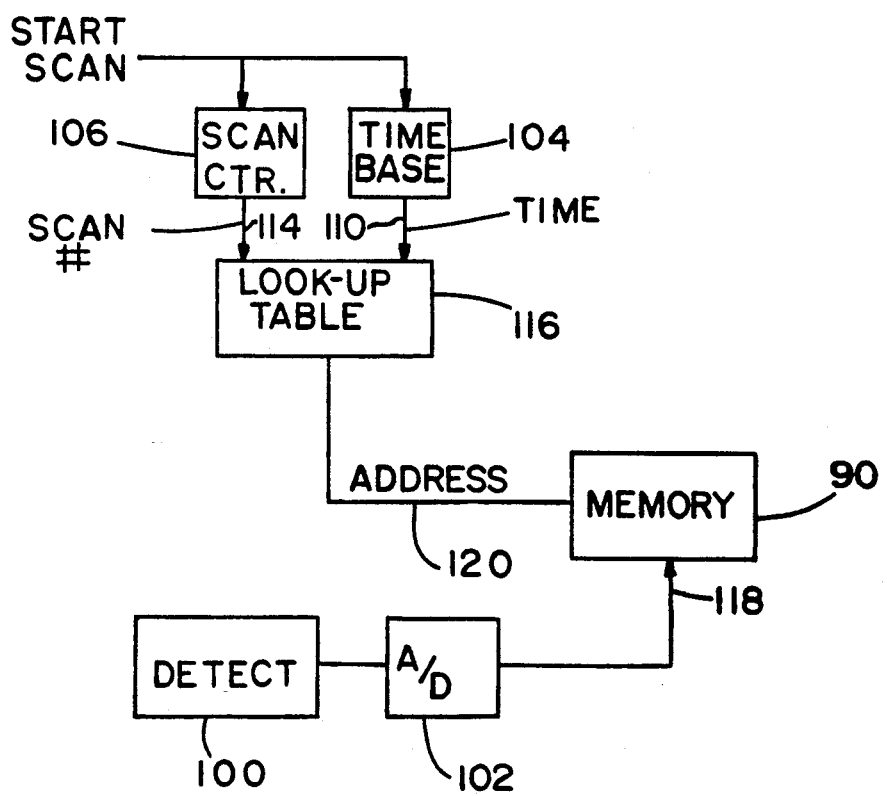
FIG. 6 is a block diagram of an addressing network.

After the memory has been loaded in the manner shown in FIGS. 5 and 6, it is a simple matter to read the contents out to a display in conventional row by row fashion to produce a proper display of the required image information. Of course, it is also within the scope of the invention to read each scan line into the memory in conventional vertical or horizontal line by line fashion, and to perform the "straightening" of the image information when the contents of the memory are read out to a display, or to not use a memory at all, but rather to directly address a display with "straightened" image information, e.g., in the same manner as memory 90 is addressed in FIG. 6.

There thus has been disclosed a method and apparatus for providing image information with a flying spot scanner of reduced mass. While the invention has been illustrated by illustrative and preferred embodiments, variations will be apparent to those skilled in the art. For example, flying spot scanners which produce curved scanning lines which are not arcuate may be provided.

It therefore should be understood that the invention is to be construed as embracing each and every novel feature and combination of novel features present in or possessed by the method and apparatus disclosed herein, and should be limited only by the claims appended hereto.

I claim:

1. A method of creating image information corresponding to an object which is inspected with penetrating radiation comprising, scanning said object with a flying spot of penetrating radiant energy along arcuate lines, detecting said radiant energy after interaction with said object, and as a result of said detecting, forming a detection signal, producing pixels from said detection signal, wherein each pixel corresponds to an elementary frontal area of the object, and feeding said pixels, or signals derived therefrom, to a utilization means in such manner that the pixels which correspond to a scan line of said object define an arcuate line in the utilization means.

2. The method of claim 1 wherein said utilization means comprises a memory.

3. The method of claim wherein said utilization means comprises a display device.

4. An apparatus for creating image information corresponding to an object which is inspected with penetrating radiant energy, comprising, means for scanning said object with a flying spot of penetrating radiant energy along arcuate lines, radiant energy detecting means for receiving said radiant energy after interaction with said object and providing at least one detection signal, means for producing pixels from at least one detection signal, wherein each pixel corresponds to an elementary frontal area of the object, and means for feeding said pixels, or signals derived therefrom, to a utilization means.

5. The apparatus of claim 4 wherein said means for feeding said pixels or signals derived therefrom to a utilization means comprises means for feeding said utilization means in such manner that the pixels which correspond to a scan line of said object define an arcuate line in said utilization means.

6. The apparatus of claim 5 wherein said radiant energy detecting means comprises a transmission detector having a shape which corresponds to said arcuate lines.

7. The apparatus of claim 5 wherein said radiant energy detecting means comprises a detector of scattered radiation.

8. The apparatus of claim 5 wherein said means for scanning said object with a flying spot of radiant energy comprises a source of penetrating radiation, an absorber plate having a fixed slit in the shape of an arc, and an absorbing chopper wheel having at least one radially oriented slit.

9. The apparatus of claim 8 wherein said means for scanning said object with a flying spot of radiant energy further comprises means for effecting relative translation movement between said and object and said fixed slit in said absorber plate.

10. The apparatus of claim 5 wherein said utilization means comprises a storage means.

11. The apparatus of claim 5 wherein said utilization means comprises a display means.

12. An apparatus for scanning a object with penetrating radiation, comprising, a source of penetrating radiation, an absorber plate having a fixed, arcuate slit therein, a chopper wheel made in part of radiation absorbing material, the chopper wheel having at least one radially oriented slit therein, the source of penetrating radiation, the absorber plate, and the chopper wheel being positioned with respect to each other so that radiation from the source passes through the fixed slit in the absorber plate and is incident upon the chopper wheel, and means for rotating the chopper wheel.

13. The apparatus of claim 12 wherein the chopper wheel has an annular ring shaped portion of radiation absorbing material, and the radial slits are in such portion.

14. The apparatus of claim 13 wherein the radiation from the source which passes through the fixed slit in the absorber plate is projected substantially wholly upon the annular ring shaped absorbing portion of the chopper wheel.

15. The apparatus of claim 12, further comprising means for effecting relative translation motion between said object and said fixed slit in said absorber plate.

16. A method of creating image information corresponding to an object which is inspected with penetrating radiation comprising, scanning said object with a flying spot of penetrating radiant energy along curved scanning lines, detecting said radiant energy after interaction with said object, and as a result of said detecting, forming a detection signal, producing pixels from said detection signal, wherein each pixel corresponds to an elementary frontal area of the object, and feeding said pixels, or signals derived therefrom, to a utilization means in such manner that the pixels which correspond to a scan line of said object define a curved line in said utilization means which has the same shape as said curved scanning lines.

* * * * *